(12) United States Patent
Gibson et al.

(10) Patent No.: US 7,569,743 B2
(45) Date of Patent: Aug. 4, 2009

(54) LETTUCE BREEDING METHOD

(75) Inventors: George D. Gibson, Prunedale, CA (US); Nathan K. Olivas, Carmel Valley, CA (US); Peter Salm, Capitola, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 11/818,736

(22) Filed: Jun. 15, 2007

(65) Prior Publication Data

US 2008/0072353 A1 Mar. 20, 2008

Related U.S. Application Data

(60) Provisional application No. 60/814,641, filed on Jun. 15, 2006.

(51) Int. Cl.
*A01H 1/00* (2006.01)
(52) U.S. Cl. .................. 800/271; 800/274
(58) Field of Classification Search .................. None
See application file for complete search history.

(56) References Cited

U.S. PATENT DOCUMENTS

| 6,689,941 B2 | 2/2004 | Waycott |
| 2005/0102718 A1 | 5/2005 | Waycott |

FOREIGN PATENT DOCUMENTS

JP 2005-110623 A 4/2005

OTHER PUBLICATIONS

Fehr 1987, Principles Of Cultivar Development vol. 1 Theory and Technique, McGraw-Hill Inc. New York, pp. 518 and 520.*
Allard 1960, Principles of Plant Breeding, John Wiley & Sons, Inc. New York, pp. 467 and 469.*
Goubara et al 2003, Flower visitors of lettuce under field and enclosure conditions, Appl. Entomol. Zool. 38(4): 571-581.*
Vaughan, M. et al. (2004). "Farming for Bees: Guidelines for Providing Native Bee Habitat on Farms," The Xerces Society: Portland, OR, pp. 1-34.
"Flowering and Fruiting of Plants," located at <http://gears.tucson.ars.ag.gov/book/flower.html> visited on Jun. 11, 2007. (12 pages).
"Flower-Visiting Insects of Wild Lettuce," located at <http://www.shout.net/~jhilty/plants/wild_lettuce.htm> visited on Jun. 11, 2007. (1 page).
"Pollination Services: No Food Without Them," located at <http://www.rand.org/scitech/stpi/ourfuture/NaturesServices/sec1_pollinators.html> visited on Jun. 11, 2007. (3 pages).
"Wild Lettuce: Lactuca canadensis, Aster Family (Asteraceae)," located at <http://www.illinoiswildflowers.info/prairie/plantx/wild_lettucex.htm> visited on Jun. 11, 2007. (2 pages).
Langton, F. A. et al. (1990). "Heterosis in Crisphead Lettuce (*Lactuca sativa* L.) hybrids," *Euphytica* 49:15-23.
Prakash, C. S. (Mar. 1996) "Information Systems for Biotechnology NBIAP News Report," located at <http://www.isb.vt.edu/news/1996/news96.Mar.html> visited on Jun. 21, 2007. (9 pages).
Goubara, M. et al. (2003). "Flower Visitors of Lettuce Under Field and Enclosure Conditions," *Applied Entomology and Zoology* 38(4):571-581.
Goubara, M. et al. (2004). "Pollination Effects of the Sweat Bee Lasioglossum villosulum trichopse (Hymenoptera: Halictidae) on Genic Male-Sterile Lettuce," *Applied Entomology and Zoology* 39(1):163-169.
"Appendix 1 New Zealand Horticultural Crops: Modes of Pollination and Value of Honey Bees," Literature Review on Genetically Modified Plants and Bee Products, New Zealand Ministry of Agriculture and Forestry, located at <http://www.maf.govt.nz/mafnet/rural-nz/research-and-development/biotechnology/literature-review-gm-plants-and-bee-products/gm-plants-bees-10.htm> visited on Jun. 21, 2007. (2 pages).
"Inbreeding Depression and Hybryd Vigor," Earthwood-Hand Pollination, located at <http://users.netconnect.com.au/~ewood/seedsav4.html> visited on Jun. 21, 2007. (4 pages).
International Search Report and Written Opinion mailed Aug. 12, 2008, for PCT Application No. PCT/US07/14063 filed Jun. 15, 2007, 7 pages.
International Search Report and Written Opinion mailed Apr. 16, 2009, for PCT Application No. PCT/US08/87789 filed Dec. 19, 2008, 15 pages.

\* cited by examiner

*Primary Examiner*—David H Kruse
(74) *Attorney, Agent, or Firm*—Morrison & Foerster LLP

(57) ABSTRACT

Methods for pollinating lettuce and producing hybrid lettuce seed are described. The methods include the steps of providing lettuce plants and releasing *Megachile rotundata* bees or attracting pollinators. Hybrid lettuce seeds and plants produced using methods of this invention and male sterile lettuce lines used in this invention are also described.

26 Claims, No Drawings

LETTUCE BREEDING METHOD

RELATED APPLICATION

This application claims the benefit of U.S. Provisional Application No. 60/814,641, filed Jun. 15, 2006, which is hereby incorporated by reference.

BACKGROUND OF THE INVENTION

Lettuce is a popular crop. Worldwide lettuce consumption continues to increase. As a result of this demand, there is a continued need for new lettuce varieties.

Lettuce is an obligate self-pollinating species. This means that the pollen is shed before stigma emergence, assuring 100% self-fertilization. Each lettuce flower is an aggregate of about 10-20 individual florets (typical of the *Compositae* family).

Hybrid vigor or heterosis occurs in both cross-pollinating and self-pollinating species. Typical presentations of hybrid vigor for lettuce include increased yield, head size and weight, quality, and resistance to unfavorable environmental factors. Another presentation of hybrid vigor is uniformity in maturity, which makes the variety more suitable for mechanical harvesting.

Current methods for crossing of lettuce include methods involving considerable effort. For example, anther tubes may be manually removed from flowers, which though an effective means to ensure the removal of all self-pollinating possibilities, is very tedious and time consuming when a large number of crosses are to be made. Crosses can also be made by misting the designated male flowers to wash the pollen off prior to fertilization. Pollen from another variety or donor parent is then introduced by gently rubbing the stigma and style of the donor parent to the maternal parent. Tags with the pertinent information on date and pedigree are then secured to the flowers in order to keep track. About 3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. While these methods are effective, they have multiple steps requiring tedious efforts. The structure of the lettuce flower, with a style enclosed by five fused anthers, makes manipulation particularly difficult and reduces the efficiency of these methods.

Another type of crossing method involves the use of male sterility systems. Male sterility has been engineered in lettuce by expression of a ribonuclease gene under the control of a tapetum-specific promoter. Reynaerts et al., Engineered genes for fertility control and their application in hybrid seed production, *Scientia Horticulturae* (1993) 55 (1-2): 125-129. However such lines are often not completely sterile and have abnormally shaped leaves. Other male sterile systems include the expression of beta-glucanase via a tapetum-specific promoter. Curtis et al., Genomic male sterility in lettuce, a baseline for the production of F1 hybrids, *Plant Science Limerick* (1996) 113(1): 113-119. Dr. Edward Ryder has described several male sterility systems, but each has characteristics which hinder its use commercially including less predictable segregation ratios, partially fertile "sterile plants," lack of differentiation between the sterile and fertile plants among others.

Genetically engineered sterility is also available, but is considered GMO and is not a preferred format.

Thus there remains a need in the art for lettuce hybrid production methods not requiring laborious human intervention.

BRIEF SUMMARY OF THE INVENTION

In one aspect, the invention provides methods for pollinating an emasculated cultivated lettuce plant by providing a first lettuce plant having pollen; providing at least one emasculated lettuce plant; and releasing *Megachile* bees, where the bees transfer pollen from the first lettuce plant to the emasculated lettuce plant to pollinate the emasculated lettuce plant. The emasculated plant may either be a plant that does not produce pollen or a plant where the pollen has been removed. In preferred embodiments, the emasculated plant is a plant that does not produce pollen, most preferably, a male sterile line. In other embodiments, the emasculated plant is a plant where the pollen has been removed, e.g., by anther removal or misting.

In a further aspect, the invention provides methods for pollinating an emasculated lettuce plant as described above with the additional step of attracting *Megachile* bees.

These *Megachile* bees may be attracted by positioning one or more attractors in the proximity of the lettuce plants, where the *Megachile* bees transfer pollen from the first lettuce plant to the emasculated lettuce plant. Alternatively, the *Megachile* bees may be attracted by positioning plants or plant products which attract the *Megachile* bees in the proximity of the lettuce plants. The attractor is preferably alfalfa.

In yet another aspect, the invention provides methods for producing hybrid lettuce seed. In one preferred embodiment, the method has the steps of providing a first lettuce plant having pollen; providing at least one emasculated lettuce plant; and releasing *Megachile* bees, where the bees transfer pollen from the first lettuce plant to the emasculated lettuce plant to form a pollinated lettuce plant; and growing the pollinated lettuce plant to produce hybrid lettuce seed. In another preferred embodiment, the method has the steps of providing a first lettuce plant having pollen; providing at least one emasculated lettuce plant; and attracting *Megachile* bees to the first lettuce plant, where the *Megachile* bees transfer pollen from the first lettuce plant to the emasculated lettuce plant to form a pollinated lettuce plant; and growing the pollinated lettuce plant to produce hybrid lettuce seed.

In still yet another aspect, the invention provides methods for pollinating an emasculated lettuce plant having the steps of: providing a first lettuce plant having pollen; providing at least one emasculated lettuce plant; and attracting *Megachile* bees to the first lettuce plant, where the *Megachile* bees transfer pollen from the first lettuce plant to the emasculated lettuce plant and form a pollinated lettuce.

In preferred embodiments of methods of this invention, the *Megachile* bee is *Megachile rotundata*, *Megachile relativa*, or *Megachile pugnata*. The first lettuce plant can be an inbred or F1 line. In preferred embodiments, the emasculated plant is a male sterile breeding line (also known as female line). The lettuce plants are preferably iceberg, romaine, redleaf, butter, serriola or greenleaf cultivars.

The release of the *Megachile* bees can be performed in an open field or an enclosed area. The bees may be released in batches on a weekly basis, e.g., 50,000 or 100,000/batch. In preferred embodiments, the step of releasing is performed in a climate that reaches at least about 74° F. during the time that the lettuce flower bloom.

In other aspects, the invention provides hybrid lettuce seed. In one preferred embodiment, the hybrid lettuce seed results from a cross between a first lettuce plant having pollen and an emasculated lettuce plant, where the cross (pollination) is performed by a process having the steps of releasing *Megachile* bees, where the bees transfer pollen from the first lettuce plant to the emasculated lettuce plant to form a pollinated lettuce plant; and growing the pollinated lettuce plant to produce hybrid lettuce seed. In another preferred embodiment, the hybrid lettuce seed results from a cross between a first lettuce plant having pollen and an emasculated plant, where the cross is performed by a process having the steps of attracting *Megachile* bees, where the *Megachile* bees transfer pollen from the first lettuce plant to the emasculated lettuce plant to form a pollinated lettuce plant; and growing the pollinated lettuce plant to produce hybrid lettuce seed.

Emasculated lettuce plants can be provided by transplanting emasculated lettuce plants, transplanting lettuce plants and emasculating them or by planting seeds which germinate and grow into emasculated lettuce plants or plants that can be emasculated. Plants having pollen can be provided by transplanting lettuce plants with pollen, transplanting lettuce plants which grow to produce pollen or by planting seeds which germinate into emasculated lettuce plants.

DETAILED DESCRIPTION OF THE INVENTION

Definitions

As used herein, the term "lettuce" refers to any cultivated member of the *Lactuca* genus including *Lactuca sativa* L. and *Lactuca serriola* species. Lettuce does not refer to wild lettuce, *Lactuca Canadensis*.

As used herein, the term "releasing" refers to any act requiring human intervention which results in movement of bees from a space lacking cultivated lettuce plants to one with cultivated lettuce plants present.

As used herein, the term "positioning" refers to the placement of plants and or plant-derived products at a distance from lettuce plants that is short enough to attract *Megachile* bees and increase the frequency of pollination of lettuce plants.

As used herein, the term "proximity" refers to being within a sufficiently small distance from lettuce to attract *Megachile* bees and increase the frequency of pollination of lettuce plants.

As used herein, the term "attracting" refers to any act which is conducted with the purpose of or the effect of increasing the number and/or concentration of lettuce pollinators near lettuce plants.

The term "emasculated" refers to cultivated lettuce plants where pollen is removed or not produced. Lettuce may be emasculated via methods known in the art, including classical breeding to develop male sterile plants, engineered male-sterility, anther tube removal, and pollen washing. Such emasculated plants are also known as male sterile plants or female plants. It is understood that cultivated male sterile lettuce plants may produce a small amount of pollen. Such plants may produce a small amount of seed via self pollination.

Methods for Pollination and Hybrid Lettuce Seed Production

The present invention provides methods for pollinating emasculated cultivated lettuce plants and producing hybrid lettuce seeds.

Lettuce

The lettuce plants of this invention can be any cultivated member of the *Lactuca sativa* or *Lactuca serriola* species capable of being pollinated by methods described herein. Preferred lettuce types include iceberg, romaine, green leaf, red leaf, butter and serriola.

In preferred embodiments of the methods described herein seeds of cultivated lettuce plants capable of producing pollen and lettuce plants incapable of producing pollen or plants from which pollen will be removed prior to pollination (emasculated or to be emasculated lettuce plants) are planted in the vicinity of one another to enable the production of hybrid lettuce plants through use of the pollination procedures described herein. The lettuce plant capable of producing pollen and used to donate pollen can either be an inbred line or an F1 line and can be any species of *Lactuca sativa* or *Lactuca serriola* with characteristics that are desired in a hybrid plant or with a genotype that is expected to produce a hybrid plant with desired characteristics.

The emasculated lettuce plants are lettuce plants where pollen is removed or not produced. Pollen can be removed by removing the anthers or misting the anthers to wash off pollen. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma will be visibly open in a "V" shape. Anthers can be removed using any method known to those of skill in the art. One method is to pinch the side of the anther cone of an unopened flower with tweezers and pull the anther straight out.

Lettuce lines which do not produce pollen (or produce insignificant amounts of pollen) can also be utilized to produce hybrid lettuce seeds and plants. Such emasculated plants can be a male sterile lettuce plant. The male sterility may be cytoplasmic, genetic, cytoplasmic-genetic, functional, or result from self-incompatibility. Such emasculated plants are also known as female lettuce plants or male sterile plants. Plants that produce pollen are also known as male plants. Male sterile lettuce lines are available. For example, the male sterile line MS7 X Salinas 88, BC4 is available from Dr. Edward Ryder at the USDA Salinas Calif. research facility. MS7 was first described in Ryder, Genetic Studies in Lettuce (*Lactuca sativa* L.), *J. Amer. Soc. Hort. Sci.* (1971) 96(6): 826-828.

MS7 X Salinas 88, BC4 can be utilized to produce additional male sterile lines via crossing with cultivated lettuce varieties. For example, iceberg, romaine, redleaf, serriola or green leaf cultivated lettuce types can be crossed with MS7 X Salinas 88, BC4 to produce F1 seed. In one embodiment, F1 seed is planted and cuttings are taken and maintained in tissue culture. Sterile plants are identified at the flowering stage. Sterile plants are increased in tissue culture. The tissue cultured plants are transferred to soil where the plants are grown to the flowering stage and then crossed with pollen-producing flowers to produce seed. Seed is harvested. The harvested seed is planted and the resulting plants are further selected and rogued for uniformity and the desired traits. Additional back crossing can be performed to increase the homozygosity of the male sterile mother lines. This process can be repeated. Once such male sterile lines are stable and uniform, they can be used as male sterile plants to produce hybrid lettuce seed by crossing with pollen-producing inbred lettuce plants using the methods described herein.

Planting of Seeds of Cultivated Lettuce Plants

In preferred embodiments, seeds of cultivated lettuce plants utilized to produce hybrid lettuce seed are planted at a sufficient distance away from other flowering crops (or at a different time) to minimize the possibility of *Megachile* bees favoring flower species over lettuce. If the *Megachile* bees were to favor flower species other than lettuce, the pollination rate for the lettuce plants could be decreased.

In preferred embodiments, the seeds of the cultivated lettuce plants are planted so that there is a higher proportion of female (emasculated or male sterile) to male (pollen-producing) plants. Lettuce plants are generally grown in rows. In certain embodiments, the ratio of male to female rows is 1 male: 1 female in alternating rows or 1 male: 2 female in rows.

Pollinators

As described in detail herein, pollination of the male sterile (female) lettuce plants is facilitated by the use of certain bees. The methods described herein include the step of releasing bees of the *Megachile* species. Preferably the bees are *Megachile rotundata*, *Megachile pugnata*, or *Megachile* relative bees. While not wishing to be bound by theory, it is believed that bees of the *Megachile* species are particularly useful for methods of this invention because aspects of its behavior allow it to effectively pollinate lettuce. For example, under preferred temperatures, the *Megachile* spp. is active during the short morning period in which lettuce flowers are open and capable of being pollinated. Furthermore, the *Megachile* spp. is a small and agile bee that does not appear to be hindered by the heavy sticky latex present on the stems and branches of the flowering lettuce plant. This small size also allows the bee to forage deep inside the small lettuce flowers, thus permitting pollination to occur. *Megachile* spp. have been observed foraging on the lettuce flowers and show no preference between male sterile or male fertile flowers. In addition, *Megachile* spp. return to their nest each evening, so that once released, they do not just fly off to another location. Furthermore, they do not communicate with each other as honey bees do, so they are less likely to leave in mass numbers in search of other more lucrative pollen/nectar sources.

*Megachile* bees are solitary bees meaning that each female lays eggs and provisions her own nest cells. Even though they are solitary, the *Megachile* bee is also a gregarious bee which means it prefers to live close to other bees of the same species.

*Megachile* bees will generally pollinate at temperatures of approximately 74 to 80° F. or above as they prefer dry sunny climates; these bees will not pollinate as well in cool cloudy or rainy weather. Rearing of *Megachile* bees is well established; the pupae are relatively low cost to purchase.

*Megachile* bees are available from International Pollination Systems Inc. who obtains such bees from commercial suppliers in Canada and the western U.S. such as Idaho. *Megachile* bees are generally delivered as late instar larvae enclosed in leaf cells. Cells are generally sold in gallon quantities with one gallon containing about 10,000 cells. High quality cells will generally result in about 80% bee emergence. The *Megachile* bee cells are generally stored in screen trays or vented pint glass jars at 40° F. (4° C.). Cells should be kept in layers of approximately 3.8 cm or less to minimize reduced bee emergence; greater cell depths allow overheating which kills larvae in the bottom layer of cells. The bee cells require about 30 day warm treatment before all bees will emerge as described at the USDA Web site on pollination. Such warm up periods are generally carried out in an incubator.

The release of bees is timed to optimize pollen transfer from one lettuce plant to another by the bees. Preferably, the bees are released at the time when the lettuce plants are mature and in the initial flowering stage. Since it takes a period of time for bees to become acclimated to the environment and become effective pollinators, the bees should be released slightly before the beginning of the optimal time period for pollination.

The bees are released in the vicinity of the provided lettuce plants. The bees may be released any distance from the lettuce plants with pollen for which the bees will travel to reach the lettuce and perform the transfer of pollen from one lettuce plant to another. This distance may be from about zero to about 200 feet from the bee hive to the plant. In certain embodiments, the distance is about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, and about 200 feet. Preferably, bee nesting boards are placed in a southward orientation to face the sun throughout the day.

The bees can be released in any type of environment which supports the growth of the lettuce plants and the movement of the bees for a time sufficient to transfer pollen. Typical environments for release include an open field or an enclosed space, such as a screened cage or a greenhouse. The temperature of the environment is one that reaches at least approximately 74° F. during the time that the lettuce flowers bloom.

In all environments, the conditions should be such that the bees are likely to transfer pollen from one lettuce plant to another rather than between other plants of other species. Preferably, the site of bee release is located away from other plants attractive to the bees and/or the site of release is a location with a low proportion of other plants attractive to the bees.

The number and frequency of bees released should be such that the density of bees is high enough to ensure sufficient pollination to achieve fertilization. Preferably, the density is high enough to generate sufficient F1 lettuce seed. Preferably, the density of bees is approximately 100,000 bees/acre. If the density of bees drops below the desired level, then additional bees can be released.

The preferred frequency of release will vary depending on the particular environment. For example, in screen cage and field conditions, the bees are preferably released in batches on a weekly basis. The number of bees released will also vary depending on the particular environment. For example, when bees are released in an open field of roughly 2 acres, a population of at least approximately 200,000 *Megachile* bees should be maintained throughout the flowering cycle.

Hybrid Lettuce Seed

Male sterile lines may be utilized in the development and breeding of hybrid lettuce varieties. The male sterility (lack of pollen) of the female parent minimizes competition between self and foreign pollen, thus increasing the rate of production of F1 hybrid seed. The F1 seed is produced as the pollen from the male parent (pollen producing plant) is transferred via *Megachile* bee to the pollen-free stigmas of the female (male sterile) parent.

In one embodiment, a field is planted with alternate rows of seeds of male fertile and male sterile lettuce plants. The lettuce plants are grown, allowed to bolt, and flower. At the first stages of flowering the male sterile rows are rogued and the segregating male fertile plants are removed from the rows containing male sterile lines. The male fertile plants are identified by the presence of pollen inside the composite flower. In one format, the *Megachile* bee nesting boxes are placed on posts, elevated from the ground the edge of the field, with the nest tube openings facing south. In one format, a nesting box is placed approximately every 100 feet along the north side of the field. The first release of *Megachile* bees is generally designed to obtain a population of bees equivalent to 100,000 *Megachile* bees per acre. Additional *Megachile* bees can be released to maintain this population throughout the flowering period of the male sterile plants. Once flowering significantly subsides in the male sterile plants, the male fertile plants are removed from the field to prevent seed contamination. Once the seed is set and the plants have dried sufficiently, the F1 seed produced is harvested from the male sterile lettuce flowers. The F1 seed is cleaned and processed and planted to produce F1 hybrid lettuce plants.

The use of a male sterile line eliminates the need to emasculate one of the parents in order to reduce selfing. For example, instead of washing pollen from stigma and manually transferring pollen to the de-pollinated maternal parent, hybrid seed production can be achieved in a single step by transferring pollen to a male sterile parent either manually or by use of *Megachile* bees. In one embodiment, hybrid lettuce plants are produced by providing an inbred male sterile line as described herein and another inbred pollen producing line and releasing *Megachile* bees to transfer pollen from the inbred pollen producing male parent to the male sterile female line.

In one embodiment, the invention is a hybrid lettuce seed and plants produced therefrom resulting from use of the herein described methods. A lettuce plant having pollen and an emasculated plant are provided and *Megachile* bees are released. Pollen is transferred from the lettuce plant with pollen to the emasculated plant by the bee. Fertilization produces F1 hybrid seeds. Hybrid lettuce plants are grown from these F1 seeds.

F1 hybrid lettuce plants are those lettuce plants produced from the first filial generation after flowers from 2 genetically different parent lines are cross pollinated. In preferred embodiments, the hybrid lettuce plants are those with improved growth parameters as compared to the parent plant, or hybrid vigor. Most preferably, the hybrid lettuce plants are those with an increase in average head weight over the parent lines. The increase in head weight can be about 110%, about 100%, about 90%, about 80%, about 70%, about 60%, about 50%, about 40%, about 30%, about 20%, or about 10%. In other embodiments, the plants are those with improved per acre head yield or increased fresh weight in terms of pounds or tons total.

Attraction of *Megachile* Bees in Order to Produce Hybrid Plants

Methods of pollinating lettuce and producing hybrid lettuce which include the step of attracting *Megachile* bees are also provided. The step of attracting *Megachile* bees may be the only step in the method or may one of several steps in the methods of pollinating cultivated lettuce. For example, a method for pollinating lettuce can include releasing *Megachile* bees, attracting *Megachile* bees or a combination thereof.

*Megachile* bees can be attracted to lettuce by any method used by those of skill in the art to attract *Megachile* bees to a particular location. For example, plants which are known to be attractive to *Megachile* bees, such as alfalfa can be grown near the lettuce. Alternatively, products derived from the plant containing the components of the plant which attract the *Megachile* bees can be placed near or in contact with the lettuce plant. When the lettuce plants flower, the alfalfa plants can be disked down or the plant products removed so that the *Megachile* bees will focus on the lettuce plants. Such products can also be sprayed on the lettuce plants. Wild *Megachile* bees can also be attracted by creating an environment that is attractive to them, such as nesting boards or tubes for nesting.

In one embodiment, a field is planted with alternate rows of seeds of male fertile and male sterile lettuce plants and hedging rows of alfalfa in order to attract *Megachile* bees. The lettuce plants are grown, allowed to bolt, and flower. At the first stages of flowering, the male sterile rows are rogued and the segregating male fertile plants are removed from the rows containing male sterile lines. The male fertile plants are identified by the presence of pollen inside the composite flower. Once flowering significantly subsides in the male sterile plants, the male fertile plants are removed from the field to prevent seed contamination. Once the seed is set and the plants have dried sufficiently, the F1 seed produced is harvested from the male sterile lettuce flowers. The F1 seed is cleaned and processed and planted to produce F1 hybrid lettuce plants.

The description will be better understood by reference to the following Examples. All of the references cited herein are hereby incorporated by reference.

EXAMPLES

Example 1

Comparative Study of Potential Lettuce Insect Pollinators

The following insect species were tested for potential effectiveness in foraging and pollinating lettuce flowers:

| Common name | Genus/species |
| --- | --- |
| Alfalfa leafcutting bee | Megachile rotundata |
| Leafcutter bee | Megachile relativa |
| Mason bee | Osmia californica |
| Blue bottle fly | Calliphora vomitoria |
| Bumble Bee | Bombus impatiens |
| Bumble Bee | Bombas impatiens male |
| Honey bee | Apis mellifera |

The following native bee species were observed foraging on lettuce flowers:

| Genus/Species | Description |
| --- | --- |
| Anthophora urbana | (large, gray and white, fast flying bee) |
| Melissodes sp. | (small, dark colored bee) |
| Agapostemon sp. | (metallic green bee - species name to be determined) |

Insect pollination experiments were conducted on flowering male fertile and male sterile lettuce plants in cage and in open field conditions. These trials were generally limited to plots or cages containing 50 flowering plants or less. In each plot a series of insect species were released and observed in the mornings. Morning activity of the insects is important as the lettuce flowers are typically only open for approximately 1 to 2 hours of each morning for some period between 7 am and 12:30 pm. The flowering time period and the duration of time a flower remains open is dependent on the climate conditions and the specific lettuce variety.

The insects released and observed were the *Megachile* relative leafcutter bee, the *Bombas impatiens* male drone bumble bee commercially known as "Macho Pol," *Apis mellifera* common honey bee, and *Calliphora vomitoria* species of Blue bottle fly. The activity of the insects was observed in a caged environment as well as in the open field. During these summer experiments no consistent pollination, foraging, or even remote interest in the lettuce flowers was noted by any species of insect observed. In open field observations no insects were observed visiting the lettuce flowers. In the caged experiments, we observed similar results and the majority of the insects were observed trying to escape from the cage. All Year Two summer insect pollination experiments were conducted at a secluded research facility in the Salinas Valley of California.

Example 2

Larger Scale Comparative Study of Potential Lettuce Insect Pollinators

These same experiments from Example 1 were repeated on a larger scale. An approximate ½ acre of lettuce was planted and allowed to flower in a remote research facility in Santa Cruz county, California. The insects released and observed were the *Megachile rotundata* alfalfa leafcutter bee, the *Bombas impatiens* male drone bumble bee, *Apis mellifera* honey bee, and *Calliphora vomitoria* species of Blue bottle fly. These same insects were also observed in a caged situation. Again, based on our field and cage observations, none of the insect species released showed any interest foraging or pollinating the lettuce flowers. The *Megachile rotundata* was never observed flying as they did not emerge from their tubes.

Example 3

Comparative Study of Potential Lettuce Insect Pollinators in a Warmer Climate: Cage and Field Studies Though the climate of the central California coastal region is ideal for commercial lettuce production, it appears to be too cool for ideal lettuce seed production. Upon further research it was determined that ideal insect activity requires higher temperatures, which was especially evident with the *Megachile* bees.

As such, pollination research was relocated to the warmer climate of the San Joaquin valley. Open field and caged pollination experiments were again conducted on a larger scale using both male fertile and male sterile flowering lettuce plants. Two and a half acre adjacent plantings of lettuce plants were transplanted in the spring and summer of Year Four. The first acre and a half was transplanted in early May and the second in mid-June. The staggered plantings were important to lengthen the time that there would be flowering plants to observe. Each planting had plots on alternate beds of male sterile plants. These plots contained roughly 100 plants each and were located at random throughout the field. Each plot of male sterile plants had a row of male fertile plants on both sides. The male sterile lines used in the experiment segregate 50/50 for fertility so the plots were rogued daily at first flowering for the presence or absence of pollen. Any plant within a male sterile plot that contained pollen was removed.

In this same production area, two 10 ft×10 ft×8 ft cages were erected and filled with roughly 50 potted lettuce plants each. Each cage contained 25 male sterile plants and 25 male fertile plants.

The following observations were made and recorded at the production locations:

Screen Cage Studies

Alfalfa Leafcutting Bee: Incubation of 5,000 alfalfa leafcutting bees (*Megachile rotundata*) was initiated on June 13 in a wood nest board. A second batch of 5,000 alfalfa leafcutting bee (ALB) was started June 28 of the same year. The first batch was released in a screen cage on July 12 in the West Cage. The second batch was released in an adjacent cage on July 20 in the East Cage. Incubation temperatures ranged from 62 to 98° F. Male bees began to emerge after 376 degree days (base 60° F.) for the first board and 384 degree days for the second board.

Male and female alfalfa leafcutting bees were observed visiting flowers. Females probed flowers with their tongues, rotating around the flower. After visiting several flowers, females often paused to groom themselves for several minutes which was probably because of the latex exuded by the plants.

On July 16 two female alfalfa leafcutting bees were observed visiting flowers. They each averaged 11.5 seconds spent on each flower (n=9), with a range from 4.2 to 25.0 seconds spent on a flower. On July 23 alfalfa leafcutting bees were observed for 2 minute intervals and averaged 4.6 flowers visited per minute (n=10).

On August 24 male sterile flowers that had been tagged after being visited by an alfalfa leafcutting bee (ALB) were examined for seed set. Flowers visited by an ALB female averaged 5.6 seeds (n=16, range 0-18) and flowers visited by an ALB male averaged 10.0 seeds (n=4, range 0-17).

The west cage was finished blooming around July 21 and the east cage was finished around July 30. The east cage was modified with extra shade cloth on half the cage (west side) and the addition of potted lavender plants to provide some additional bloom for pollinators late in the day. These efforts appeared to increase the lifespan of the leafcutting bees in the cages.

Osmia californica: Osmia californica is a native species that visits many species of composites. Reeds containing diapausing adults were obtained from a source in Utah. A test incubation of 5 reeds showed that males began to emerge after 2 days of incubation. Females began to emerge after 6 days. In those 5 reeds, there were a total of 36 bees (7.2 per reed). 19 of those emerged (52%). Partial emergence is normal for this species with some emerging the first year, and the rest emerging the following year.

20 reeds (ca. 144 bees) of O. californica were released in the west cage on July 12 of Year Four. On July 16 of Year Four, 40 reeds (ca. 288 bees) were installed in the east cage. On July 14 of Year Four one O. californica was observed visiting flowers. O. californica bees were found dead in the cages, so some bees emerged, but survival in the cages was poor.

Blue bottle fly: Blue bottle fly (Calliphora vomitoria) pupae were obtained from Idaho. On July 23 of Year Four, 3 cups of pupae (5100 flies) were placed in the east cage, and one cup (1700 flies) was placed in the west cage. Flies were observed in the cages on July 25 of Year Four but only rarely visited flowers. When they were seen on flowers, they did not appear to be probing for nectar. They appeared disinterested and ineffective as pollinators in a large cage.

Bumble Bees: One class C bumble bee colony (Bombus impatiens; Natupol) was obtained and attached to a fence post in the east cage on July 23. The bumble bees were observed flying around the cage and survived for the duration of the trial, probably subsisting on the food supplied with the colony. On occasion bumble bees could be observed visiting flowers and a few bumble bees were observed with pollen loaded on the hind legs. On July 30 of Year Four, one bumble bee with pollen on its legs was observed visiting 27 flowers in 2 minutes (13.5 flowers per minute). However, it only visited male fertile flowers. Most of the bumble bees were found trying to escape from the cage.

Field Studies

A. Urbana: A. urbana was observed at the San Joaquin valley field site. On September 29, one individual was observed visiting 9 flowers in 40 seconds (13.5 flowers per minute).

Melissodes sp: Mellisodes individuals were found in the San Joaquin valley site. On August 24, one individual was observed visiting 9 flowers in 2 minutes (4.5 flowers per minute).

Honey Bee: 60 Honey bee colonies were located next to the San Joaquin valley site (3 acres). Despite the large population, the amount of foragers in the lettuce field was sparse. On September 29 honey bees were observed visiting 15.6 flowers per minute on average (n=3, range 10.3-19.5 flowers per minute).

Alfalfa leafcutting bee: ALBs were introduced into 3 shelters along the north edge of the field facing south. 5,000 bees were released on August 31, September 7, September 10, and September 22. These batches of ALBs had been incubated for 20, 20, 16 and 21 days respectively. The ALBs were observed foraging on lettuce flowers and females returned to the nesting shelter with cut leaves and pollen. The densities found in the field were sparse, however. On September 29, ALBs were found visiting an average of 3.7 flowers per minute (n=4 (2 males and 2 females), range 3.0-4.7 flowers per minute). The male fertile plants tended to close their blossoms earlier than the male sterile plants. After the male fertile plants were closed, it was not difficult to find male and female ALBs foraging on the open male sterile flowers.

O. californica: Approximately 75 reeds (280 bees) were placed in the field on August 31, September 7, September 10, and September 22 of Year Four. No O. californica were observed nesting or foraging.

Blue bottle fly: Blue bottle fly pupae were released in the ALB shelters on the same dates at the ALB releases. No blue bottle flies were found foraging in the field.

Other wild species: Several species of syrphids were found foraging in the field. Also Alfalfa butterflies (Colias euytheme) were abundant and visited lettuce flowers.

Summary

Alfalfa leafcutting bees showed that they will forage vigorously on lettuce flowers, including male sterile flowers in both screen cage and field situations. For best results, ALBs should be introduced in batches on a weekly basis. In the field, larger numbers should be used (e.g. 50,000 or more per acre) and it will be preferable to locate the field away from other attractive plants.

Example 4

Production of Male Sterile Lines

Two hundred and fifty seeds of line MS7 X Salinas 88, BC4 were obtained from Dr. Edward Ryder at the USDA Salinas Calif. research facility. MS7 was first described in Ryder, Genetic Studies in Lettuce (Lactuca sativa L.), J. Amer. Soc. Hort. Sci. (1971) 96(6): 826-828.

Monument, Sun Devil and Icon lettuce seed is commercially available from Progeny Advanced Genetics. Seed of Monument, Sun Devil, Icon, and other Progeny Advanced Genetics lettuce varieties were grown to the flowering stage and crosses were made to MS7 X Salinas 88, BC4 plants to produce Monument, Sun Devil, Icon and other male sterile F1 seed.

Monument, Sun Devil and Icon F1 male sterile seed were planted. Monument, Sun Devil, and Icon male sterile plants were grown and cuttings were taken and maintained in tissue culture. Sterile plants were identified at the flowering stage. Sterile plants were then increased in tissue culture. The tissue cultured plants were transferred to soil where the plants were grown to the flowering stage and then back crossed with Monument, Sun Devil and Icon pollen from pollen producing Monument, Sun Devil, Icon and other corresponding pollen-producing plants to produce seed. Seed was harvested.

The harvested seed was planted and the resulting plants were further selected and rogued for uniformity and the desired traits. Additional back crossing to the Monument, Sun Devil, Icon and other lines was performed to increase the homozygosity of the male sterile mother lines to produce BC1, BC2, BC3, BC4, BC5 (BC=backcross) seed.

Example 5

Additional Studies of *Megachile* Pollination of Lettuce Plants

As described in Example 3, *Megachile* bees are capable of pollinating lettuce seed in a screen cage. It was not clear if *Megachile* bees could be used effectively in an open field. As such, experiments were conducted to determine if *Megachile* bees would pollinate hybrid lettuce seed in the open field and what levels of bees would be needed to provide good seed set.

Male sterile lines were developed as outlined in Example 4. Seeds from male sterile and male fertile lines were planted and grown to the seedling stage. Male sterile and male fertile seedlings were transplanted in a field in the San Joaquin Valley of Calif. and in San Juan Bautista, Calif. This planting covered 8 rows running east to west which alternated male sterile and male fertile rows. The north 2 rows were planted with male fertile plants followed by a row of male sterile plants. Rows 4 and 5 consisted of male fertile plants, rows 6 and 7 were male sterile. Row 8, the southern most row was planted with male fertile lettuce plants. Again, the male sterile lines segregated 50/50 for male fertility. At the early flowering stage the sterile rows were rogued and pollen producing plants were removed.

The study sites were located in the San Joaquin valley and in San Juan Bautista, Calif. The San Joaquin valley field site consisted of a one acre field in a strip of 8 rows, 30 inches apart. A 100 foot section of this field was caged (2000 square feet or 0.046 acres). The San Juan Bautista site consisted of two 144 square foot cages (0.0066 acres). 500,000 *Megachile* bees were provided by International Pollination Systems Inc. from Idaho who purchased the bees from sources in Canada. 270,000 of these were loose cells, and 230,000 were in wooden nest boards.

Bee Preparation

A 30 ft×100 ft×7 ft cage was constructed in a portion of the field to contain the test insects. The cage covered 100 feet of the entire 8 row planting. Additional *Megachile* bees were introduced and the following observations were made.

The bees arrived in California on April 19. The wooden boards were stored at ambient temperatures in a garage, while the loose cells were stored in a refrigerator.

The *Megachile* bee (alfalfa leafcutting bee) has a developmental threshold of 60° F. In other words, if the cocoons are held below 60° F., the bees will stay dormant and above 60° F., the bees begin to develop. The optimum temperature for initiating development of alfalfa leafcutting bees is 86° F. One full day at 86° C. provides the bees with 26 degree days. Relative to the alfalfa leafcutting bee (ALB,) a degree day is the number of days they are at or above the incubation temperature of 60 degrees F. At 86° F., ALB males require an average of 19.4 days (504 degree days), while females require an average of 21.5 days (559 degree days) to emerge.

Before the wooden boards were moved into the bee incubation room on May 6, they had accumulated approximately 160 degree days or 6.2 days of incubation. The bee incubation room was equipped with two small air conditioning units capable of keeping the room under 66° F. in July when outside temperatures frequently reach 105° F. It was thought that the bees could be kept at these temperatures, gradually accumulating degree days until a week or so before they were needed, and then could be warmed to finish incubating at that time.

*Pteromalus* parasites began to emerge on May 20 (an indicator of around day 7 of incubation at 86° F.) and *Megachile* bees began to emerge on June 2 (an indicator of day 12 of incubation). The first male alfalfa leafcutting bee (ALB) was found on July 6 (an indicator of day 16). The first bees were removed from the incubator on August 29 (4600 bees for San Juan Bautista).

Bee Release in Field and Cage

On August 31, a hundred thousand bees were released at the San Joaquin valley site in 8 shelters, 2 of which were located inside the screen cage. On September 2, another 100,000 bees were delivered to the San Joaquin valley site. At that time, the remaining wooden boards were sampled and very few live bees were found. Most had already emerged and died inside their holes or on the floor of the incubator.

On September 3, 135,100 bees from the loose cells were brought to the San Joaquin valley. 101,300 were released in the field and 33,800 were released in the cage. This was sooner than planned for these bees, but at this time very few bees were expected to hatch from the wooden boards. These bees were shipped from Idaho International Pollination Systems Inc at a later date than the other bees and had warmed up prematurely in Idaho and it was estimated that 20 to 30% of them were lost. These bees began to emerge quickly and it was soon easy to find male and female bees in the field, on flowers and returning to nests in the shelters.

By September 7, however, few of the released bees were active. It was decided at this time to cut back two large patches of lettuce outside the cage and the entire area inside the cage in order to set back the plants so they would bloom in one to two weeks.

On September 14, 113,700 bees were released (96,300 in the field and 17,400 in the cage). Also, 5400 bees were released in each of the San Juan Bautista cages.

On September 19, 10,700 bees were added to the field and 4,000 were added to the cage in the San Joaquin valley. The bees released on September 14 and 19 had the best pre-incubation and incubation conditions and therefore were expected to have the best flight and pollination activity from these releases. On September 28, flight activity was observed to be excellent, and multiple ALB's were observed leaving the nests, in flight, foraging on lettuce flowers and returning to their nests with pollen, and many male and female bees could be observed visiting lettuce flowers. The ALBs did not appear to show any preference for male sterile or fertile flowers. A male sterile plant was observed around September 21 with numerous alfalfa leafcutting bees on the flowers.

On October 5, the pollinating activity of the ALBs was still excellent. 13 different ALB females were observed each for 2 minutes and found to visit an average of 7.1 flowers per minute (low=4, high=14 per minute).

A total of approximately 177,900 bees were released in the field (187,000 per acre), and 45,100 bees were released in the cage (902,000 bees per acre). A summary is provided in Table 1.

TABLE 1

| | Alfalfa leafcutting bees. | | |
| --- | --- | --- | --- |
| Date | V-Field | V-Cage | SJB |
| Sept. 3 | 70,900 | 23,700 | 0 |
| Sept. 14 | 96,300 | 17,400 | 10,800 |
| Sept. 19 | 10,700 | 4,000 | 0 |
| Total | 177,900 | 45,100 | 10,800 |
| Bees per acre | 187,000 | 902,000 | 1,636,000 |

V = San Joaquin Valley,
SJB = San Juan Bautista.

Summary of Results

Plants were observed to evaluate seed set. Hybrid seed production was observed to be excellent in both the cage and in the open field in all locations for all male sterile lines tested.

ALBs appear to be quite effective pollinators of lettuce and are not deterred by a lack of pollen on male sterile flowers.

ALBs can be used for pollination of lettuce in an open field.

Weekly releases of ALBs during bloom is an effective strategy for enhanced pollination.

A stocking rate of 100,000 bees per acre per week appears to be more than adequate for effective pollination.

ALBs must be held under 60° F. to stop development during the summer, especially if late summer releases are needed.

Example 6

Comparative Testing of Lettuce Hybrids Produced by Methods of this Invention

Hybrid seed was produced by crossing male sterile lines to inbred lines: A005 X PM5004, A006 X PM5004, A009 X PM5023. PM5023, A009 and A005 are Progeny Advanced Genetics iceberg lettuce male sterile research lines produced as described in Example 4. A006 is Monument male sterile line produced as described in Example 4. PM5004 is Cannery Row male fertile (pollen producing) line available from Seminis Vegetable Sees.

The hybrid seed was produced in an open field seed production crop in the San Joaquin Valley. The field was planted with alternating rows of male fertile and male sterile lettuce plants. Leaf cutting bees were released on 3 different occasions during the month long flowering period. Bee shelters were placed at multiple areas through out the field, and a combination of wood and Styrofoam boards, and loose cells containing the leaf cutting bees were placed in the shelters. Additional boards and loose cells were added at 3 different times during flowering to maintain a higher population of active leaf cutters. The leaf cutters emerged from their nests generally mid morning, after the temperatures had reached about 74 degrees, and the lettuce flowers had been open for roughly an hour. The leaf cutters were then observed to fly from their nests and shelter and to forage on both male sterile and male fertile lettuce flowers. During this foraging the leaf cutters transfered pollen from the flowers of male fertile (pollen producing) plants to the flowers of the male sterile plants. It is by this mechanism that the pollination occured and hybrid lettuce seed was produced. In about 3 weeks from the initial leaf cutter release, seed set was observed in the male sterile plants. In about 1 month following the first release of leaf cutting bees the lettuce flowering period was over and the seed was allowed to ripen. The ripe seed was harvested by hand.

Hybrid seed A005 X PM5004, A006 X PM5004, A009 X PM5023 along with their respective parents were gown for comparative analysis. Replicated trials were planted twice in the Salinas Valley of California.

The hybrids and parent varieties were replicated 3 times in each trial, 40 plants in each replication. Each plot was 20 feet in length on raised beds with 40 inch centers, 2 seed lines per bed. The plants were thinned to 12 inches. All plots were treated identically.

Ten continuous plants were cut from each plot (5 from each seed line), and the individual plants were weighed to the nearest gram and their head circumference measured to the nearest ¼ inch. The results of the studies are provided below in Tables 2-7 below.

Table 2 shows the comparative head weight and head circumference of A005 X PM5004 hybrid compared to PM 5004 parent. The results show that the A005 X PM5004 hybrid had a 33.2, 35.8 and a 37.7% increase in head weight compared to the PM 5004 parent.

Table 3 shows the comparative head weight and head circumference of A005 X PM5004 hybrid compared to A005 parent. The results show that the A005 X PM5004 hybrid had a 31.4, 29.0 and a 20.1% increase in head weight compared to the A005 parent.

Table 4 shows the comparative head weight and head circumference of A006 X PM5004 hybrid compared to A006 parent. The results show that the A006 X PM5004 hybrid had a 55.6, 52.3 and a 27.0% increase in head weight compared to the A006 parent.

Table 5 shows the comparative head weight, head circumference and core length of A006 X PM5004 hybrid compared to PM5004 parent. The results show that the A006 X PM5004 hybrid had a 36.4, 28.5, and 19.2% increase in head weight and a 26.2, 28.3 and 10.9% increase in core length compared to the PM5004 parent.

Table 6 shows the comparative head weight and head circumference of A009 X PM5023 hybrid compared to PM5023 parent. The results show that the A009 X PM5023 hybrid had a 34.1, 37.4 and 46.1% increase in head weight compared to the PM5023 parent.

Table 7 shows the comparative head weight and head circumference of A009 X PM5023 hybrid compared to A009 parent. The results show that the A009 X PM5023 hybrid had a 22.9, 31.9 and 55.7% increase in head weight compared to the A009 parent.

TABLE 2

| | | | Head Circ (in) | |
| --- | --- | --- | --- | --- |
| Rep 1 | Head Weight (g) | | A005 × | |
| Sample # | A005 × PM5004 | PM5004 | PM5004 | PM5004 |
| 1 | 1157 | 548 | 21.0 | 21.0 |
| 2 | 1227 | 965 | 20.5 | 20.5 |
| 3 | 991 | 935 | 20.0 | 21.5 |
| 4 | 1261 | 895 | 22.0 | 21.0 |
| 5 | 990 | 768 | 19.5 | 21.5 |
| 6 | 1083 | 894 | 21.0 | 21.0 |
| 7 | 1124 | 880 | 21.0 | 21.0 |
| 8 | 850 | 750 | 21.5 | 21.0 |
| 9 | 1177 | 838 | 20.0 | 20.5 |
| 10 | 1185 | 820 | 21.5 | 20.5 |
| Average | 1104.5 | 829.3 | 20.8 | 21.0 |
| Stan dev | 1.27E+02 | 1.20E+02 | 7.89E−01 | 3.69E−01 |
| T test | 9.84E−05 | | 5.93E−01 | |
| Probability % | 100.0 | | 40.7 | |
| % Difference | 33.2 | | −0.7 | |

TABLE 2-continued

| Rep 2 | Head Weight (g) | | Head Circ (in) | |
|---|---|---|---|---|
| | | | A005 × | |
| Sample # | A005 × PM5004 | PM5004 | PM5004 | PM5004 |
| 1 | 1026 | 598 | 22.0 | 20.5 |
| 2 | 1104 | 978 | 21.0 | 22.5 |
| 3 | 945 | 685 | 21.0 | 19.5 |
| 4 | 766 | 899 | 21.0 | 19.5 |
| 5 | 1169 | 740 | 20.5 | 21.0 |
| 6 | 1177 | 616 | 22.0 | 20.0 |
| 7 | 1063 | 966 | 21.0 | 21.0 |
| 8 | 1215 | 710 | 21.5 | 21.0 |
| 9 | 1166 | 852 | 21.0 | 22.0 |
| 10 | 960 | 755 | 20.0 | 21.5 |
| Average | 1059.1 | 779.9 | 21.1 | 20.9 |
| Stan dev | 1.39E+02 | 1.37E+02 | 6.15E−01 | 1.00E+00 |
| T test | 2.63E−04 | | 5.10E−01 | |
| Probability % | 100.0 | | 49.0 | |
| % Difference | 35.8 | | 1.2 | |

| Rep 3 | Head Weight (g) | | Head Circ (in) | |
|---|---|---|---|---|
| | | | A005 × | |
| Sample # | A005 × PM5004 | PM5004 | PM5004 | PM5004 |
| 1 | 1249 | 802 | 21.0 | 22.0 |
| 2 | 1016 | 1070 | 20.0 | 22.0 |
| 3 | 988 | 631 | 22.0 | 19.0 |
| 4 | 1096 | 830 | 20.0 | 20.5 |
| 5 | 930 | 751 | 20.5 | 21.0 |
| 6 | 1173 | 500 | 21.5 | 18.0 |
| 7 | 980 | 682 | 21.0 | 21.0 |
| 8 | 1080 | 791 | 21.0 | 20.0 |
| 9 | 997 | 704 | 20.0 | 21.0 |
| 10 | 1001 | 870 | 22.0 | 21.3 |
| Average | 1051.0 | 763.1 | 20.9 | 20.6 |
| Stan dev | 9.85E+01 | 1.52E+02 | 7.75E−01 | 1.27E+00 |
| T test | 8.97E−05 | | 4.98E−01 | |
| Probability % | 100.0 | | 100.0 | |
| % Difference | 37.7 | | 1.6 | |

TABLE 3

| Rep 1 | Head Weight (g) | | Head Circ (in) | |
|---|---|---|---|---|
| | | | A005 × | |
| Sample # | A005 × PM5004 | A005 | PM5004 | A005 |
| 1 | 1157 | 950 | 21.0 | 18.0 |
| 2 | 1227 | 990 | 20.5 | 20.0 |
| 3 | 991 | 870 | 20.0 | 19.5 |
| 4 | 1261 | 882 | 22.0 | 20.0 |
| 5 | 990 | 949 | 19.5 | 19.5 |
| 6 | 1083 | 655 | 21.0 | 19.0 |
| 7 | 1124 | 663 | 21.0 | 18.5 |
| 8 | 850 | 874 | 21.5 | 19.3 |
| 9 | 1177 | 644 | 20.0 | 19.0 |
| 10 | 1185 | 930 | 21.5 | 19.0 |
| Average | 1104.5 | 840.7 | 20.8 | 19.2 |
| Stan dev | 1.27E+02 | 1.34E+02 | 7.89E−01 | 6.24E−01 |
| T test | 2.71E−04 | | 7.34E−05 | |
| Probability % | 100.0 | | 100.0 | |
| % Difference | 31.4 | | 8.5 | |

| Rep 2 | Head Weight (g) | | Head Circ (in) | |
|---|---|---|---|---|
| | | | A005 × | |
| Sample # | A005 × PM5004 | A005 | PM5004 | A005 |
| 1 | 1026 | 854 | 22.0 | 21.0 |
| 2 | 1104 | 852 | 21.0 | 19.0 |
| 3 | 945 | 824 | 21.0 | 20.0 |
| 4 | 766 | 829 | 21.0 | 20.0 |
| 5 | 1169 | 916 | 20.5 | 19.5 |
| 6 | 1177 | 921 | 22.0 | 19.0 |
| 7 | 1063 | 881 | 21.0 | 19.5 |
| 8 | 1215 | 736 | 21.5 | 19.5 |
| 9 | 1166 | 729 | 21.0 | 19.5 |
| 10 | 960 | 669 | 20.0 | 19.0 |
| Average | 1059.1 | 821.1 | 21.1 | 19.6 |
| Stan dev | 1.39E+02 | 8.40E+01 | 6.15E−01 | 6.15E−01 |
| T test | 2.05E−04 | | 3.49E−05 | |
| Probability % | 100.0 | | 100.0 | |
| % Difference | 29.0 | | 7.7 | |

| Rep 3 | Head Weight (g) | | Head Circ (in) | |
|---|---|---|---|---|
| | | | A005 × | |
| Sample # | A005 × PM5004 | A005 | PM5004 | A005 |
| 1 | 1249 | 1062 | 21.0 | 20.0 |
| 2 | 1016 | 722 | 20.0 | 21.0 |
| 3 | 988 | 760 | 22.0 | 21.0 |
| 4 | 1096 | 979 | 20.0 | 21.0 |
| 5 | 930 | 790 | 20.5 | 19.0 |
| 6 | 1173 | 730 | 21.5 | 19.0 |
| 7 | 980 | 932 | 21.0 | 19.5 |
| 8 | 1080 | 1020 | 21.0 | 20.0 |
| 9 | 997 | 906 | 20.0 | 20.0 |
| 10 | 1001 | 849 | 22.0 | 19.5 |
| Average | 1051.0 | 875.0 | 20.9 | 20.0 |
| Stan dev | 9.85E+01 | 1.23E+02 | 7.75E−01 | 7.82E−01 |
| T test | 2.40E−03 | | 1.86E−02 | |
| Probability % | 100.0 | | 100.0 | |
| % Difference | 20.1 | | 4.5 | |

TABLE 4

| Rep 1 | Head Weight (g) | | Head Circ (in) | |
|---|---|---|---|---|
| | | | A006 × | |
| Sample # | A006 × PM5004 | A006 | PM5004 | A006 |
| 1 | 1415 | 866 | 22.0 | 20.0 |
| 2 | 1170 | 793 | 21.0 | 19.5 |
| 3 | 1222 | 630 | 21.5 | 19.0 |
| 4 | 1375 | 827 | 21.5 | 20.0 |
| 5 | 1391 | 868 | 22.0 | 21.0 |
| 6 | 1387 | 913 | 23.0 | 21.0 |
| 7 | 1264 | 672 | 21.0 | 20.0 |
| 8 | 1244 | 857 | 22.0 | 20.0 |
| 9 | 1264 | 1100 | 22.0 | 21.0 |
| 10 | 983 | 645 | 21.0 | 21.0 |
| Average | 1271.5 | 817.1 | 21.7 | 20.3 |
| Stan dev | 1.32E+02 | 1.42E+02 | 6.32E−01 | 7.17E−01 |
| T test | 7.10E−07 | | 1.45E−04 | |
| Probability % | 100.0 | | 100.0 | |
| % Difference | 55.6 | | 7.2 | |

| Rep 2 | Head Weight (g) | | Head Circ (in) | |
|---|---|---|---|---|
| | | | A006 × | |
| Sample # | A006 × PM5004 | A006 | PM5004 | A006 |
| 1 | 1289 | 854 | 22.0 | 21.0 |
| 2 | 1234 | 790 | 22.0 | 20.0 |
| 3 | 1278 | 770 | 22.0 | 21.0 |
| 4 | 1291 | 626 | 21.5 | 19.0 |
| 5 | 1245 | 836 | 23.0 | 20.0 |
| 6 | 1115 | 977 | 21.5 | 20.0 |
| 7 | 1330 | 964 | 20.5 | 21.0 |
| 8 | 1085 | 855 | 22.0 | 21.0 |
| 9 | 1478 | 745 | 22.0 | 19.0 |
| 10 | 1169 | 797 | 22.0 | 20.0 |

TABLE 4-continued

| | | | | |
|---|---|---|---|---|
| Average | 1251.4 | 821.4 | 21.9 | 20.2 |
| Stan dev | 1.13E+02 | 1.03E+02 | 6.26E−01 | 7.89E−01 |
| T test | 5.15E−08 | | 6.27E−05 | |
| Probability % | 100.0 | | 100.0 | |
| % Difference | 52.3 | | 8.2 | |

| Rep 3 | Head Weight (g) | | Head Circ (in) | |
|---|---|---|---|---|
| Sample # | A006 × PM5004 | A006 | A006 × PM5004 | A006 |
| 1 | 1096 | 1260 | 21.0 | 22.0 |
| 2 | 1403 | 703 | 22.0 | 19.0 |
| 3 | 1444 | 831 | 23.0 | 21.0 |
| 4 | 1036 | 1096 | 21.0 | 22.5 |
| 5 | 1211 | 690 | 23.5 | 20.0 |
| 6 | 1212 | 980 | 21.0 | 21.0 |
| 7 | 1375 | 1093 | 23.0 | 20.0 |
| 8 | 1379 | 987 | 22.0 | 21.0 |
| 9 | 1081 | 1180 | 21.0 | 21.5 |
| 10 | 1436 | 1162 | 23.0 | 22.0 |
| Average | 1267.3 | 998.2 | 22.1 | 21.0 |
| Stan dev | 1.58E+02 | 1.99E+02 | 1.01E+00 | 1.08E+00 |
| T test | 3.63E−03 | | 3.77E−02 | |
| Probability % | 100.0 | | 100.0 | |
| % Difference | 27.0 | | 5.0 | |

TABLE 5

| Rep 1 | Head Weight (g) | | Head Circ (in) | | Core Length (in) | |
|---|---|---|---|---|---|---|
| Sample # | A006 X PM5004 | PM5004 | A006 X PM 5004 | PM5004 | A006 X PM5004 | PM5004 |
| 1 | 1415 | 723 | 22.0 | 20.5 | 1.5 | 1.0 |
| 2 | 1170 | 925 | 21.0 | 21.0 | 1.0 | 1.0 |
| 3 | 1222 | 1044 | 21.5 | 20.0 | 1.5 | 1.0 |
| 4 | 1375 | | 21.5 | 20.0 | 1.3 | 1.0 |
| 5 | 1391 | 1024 | 22.0 | 21.0 | 1.0 | 1.0 |
| 6 | 1387 | 825 | 23.0 | 21.0 | 1.5 | 1.3 |
| 7 | 1264 | 1093 | 21.0 | 21.0 | 1.0 | 1.3 |
| 8 | 1244 | 928 | 22.0 | 19.5 | 1.5 | 1.0 |
| 9 | 1264 | 845 | 22.0 | 20.0 | 1.5 | 1.0 |
| 10 | 983 | 983 | 21.0 | 20.0 | 1.5 | 1.0 |
| Average | 1271.5 | 932.2 | 21.7 | 20.4 | 1.3 | 1.1 |
| Stan dev | 1.32E+02 | 1.18E+02 | 6.32E−01 | 5.68E−01 | 2.37E−01 | 1.05E−01 |
| T test | 1.82E−05 | | 1.32E−04 | | 3.56E−03 | |
| Probability % | 100.0 | | 100.0 | | 99.6 | |
| % Difference | 36.4 | | 6.4 | | 26.2 | |

| Rep 2 | Head Weight (g) | | Head Circ (in) | | Core Length (in) | |
|---|---|---|---|---|---|---|
| Sample # | A006 X PM5004 | PM5004 | A006 X PM 5004 | PM5004 | A006 X PM5004 | PM5004 |
| 1 | 1289 | 1157 | 22.0 | 21.0 | 2.0 | 1.0 |
| 2 | 1234 | 1035 | 22.0 | 23.0 | 1.5 | 1.5 |
| 3 | 1278 | 855 | 22.0 | 21.0 | 1.5 | 1.3 |
| 4 | 1291 | 954 | 21.5 | 20.0 | 1.5 | 1.5 |
| 5 | 1245 | 938 | 23.0 | 20.0 | 1.5 | 1.3 |
| 6 | 1115 | 912 | 21.5 | 20.5 | 1.8 | 1.0 |
| 7 | 1330 | 950 | 20.5 | 20.5 | 1.0 | 1.0 |
| 8 | 1085 | 992 | 22.0 | 21.0 | 2.0 | 1.0 |
| 9 | 1478 | 1027 | 22.0 | 22.0 | 1.0 | 1.0 |
| 10 | 1169 | 922 | 22.0 | 22.0 | 1.0 | 1.0 |
| Average | 1251.4 | 974.2 | 21.9 | 21.1 | 1.5 | 1.2 |
| Stan dev | 1.13E+02 | 8.39E+01 | 6.26E−01 | 9.64E−01 | 3.81E−01 | 2.11E−01 |
| T test | 7.01E−06 | | 5.47E−02 | | 2.97E−02 | |
| Probability % | 100.0 | | 94.5 | | 97.0 | |
| % Difference | 28.5 | | 3.5 | | 28.3 | |

| Rep 3 | Head Weight (g) | | Head Circ (in) | | Core Length (in) | |
|---|---|---|---|---|---|---|
| Sample # | A006 X PM5004 | PM5004 | A006 X PM 5004 | PM5004 | A006 X PM5004 | PM5004 |
| 1 | 1096 | 1286 | 21.0 | 24.0 | 1.5 | 1.5 |
| 2 | 1403 | 1050 | 22.0 | 22.0 | 1.8 | 1.0 |
| 3 | 1444 | 830 | 23.0 | 21.0 | 2.0 | 1.0 |
| 4 | 1036 | 1017 | 21.0 | 22.0 | 1.0 | 1.5 |
| 5 | 1211 | 1012 | 23.5 | 22.0 | 1.3 | 1.5 |
| 6 | 1212 | 1080 | 21.0 | 23.0 | 1.3 | 1.5 |
| 7 | 1375 | 1060 | 23.0 | 21.5 | 1.5 | 1.3 |
| 8 | 1379 | 1130 | 22.0 | 22.5 | 1.5 | 1.5 |
| 9 | 1081 | 1030 | 21.0 | 22.5 | 1.5 | 1.5 |
| 10 | 1436 | 1140 | 23.0 | 22.5 | 2.0 | 1.5 |
| Average | 1267.3 | 1063.5 | 22.1 | 22.3 | 1.5 | 1.4 |

TABLE 5-continued

| | | | | | |
|---|---|---|---|---|---|
| Stan dev | 1.58E+02 | 1.16E+02 | 1.01E+00 | 8.23E-01 | 3.22E-01 | 2.12E-01 |
| T test | 4.13E-03 | | 5.52E-01 | | 2.34E-01 | |
| Probability % | 100.0 | | 100.0 | | 100.0 | |
| % Difference | 19.2 | | -1.1 | | 10.9 | |

TABLE 6

| Rep 1 | Head Weight (g) | | Head Circ (in) | |
|---|---|---|---|---|
| Sample # | A009 × PM5023 | PM5023 | A009 × PM5023 | PM5023 |
| 1 | 1209 | 950 | 22.5 | 18.0 |
| 2 | 971 | 990 | 20.0 | 20.0 |
| 3 | 940 | 870 | 20.5 | 19.5 |
| 4 | 864 | 882 | 20.0 | 20.0 |
| 5 | 1453 | 949 | 22.0 | 19.5 |
| 6 | 1280 | 655 | 22.0 | 19.0 |
| 7 | 1412 | 663 | 22.0 | 18.5 |
| 8 | 870 | 874 | 20.0 | 19.3 |
| 9 | 1288 | 644 | 21.0 | 19.0 |
| 10 | 983 | 930 | 21.0 | 19.0 |
| Average | 1127.0 | 840.7 | 21.1 | 19.2 |
| Stan dev | 2.26E+02 | 1.34E+02 | 9.66E-01 | 6.24E-01 |
| T test | 2.88E-03 | | 4.95E-05 | |
| Probability % | 99.7 | | 100.0 | |
| % Difference | 34.1 | | 10.0 | |

| Rep 2 | Head Weight (g) | | Head Circ (in) | |
|---|---|---|---|---|
| Sample # | A009 × PM5023 | PM5023 | A009 × PM5023 | PM5023 |
| 1 | 1369 | 854 | 22.5 | 21.0 |
| 2 | 1099 | 852 | 22.0 | 19.0 |
| 3 | 1142 | 824 | 22.0 | 20.0 |
| 4 | 1007 | 829 | 21.0 | 20.0 |
| 5 | 984 | 916 | 21.0 | 19.5 |
| 6 | 1030 | 921 | 20.0 | 19.0 |
| 7 | 1205 | 881 | 22.0 | 19.5 |
| 8 | 1276 | 736 | 22.0 | 19.5 |
| 9 | 1005 | 729 | 21.0 | 19.5 |
| 10 | 1164 | 669 | 22.0 | 19.0 |
| Average | 1128.1 | 821.1 | 21.6 | 19.6 |
| Stan dev | 1.28E+02 | 8.40E+01 | 7.62E-01 | 6.15E-01 |
| T test | 5.81E-06 | | 6.14E-06 | |
| Probability % | 100.0 | | 100.0 | |
| % Difference | 37.4 | | 9.9 | |

| Rep 3 | Head Weight (g) | | Head Circ (in) | |
|---|---|---|---|---|
| Sample # | A009 × PM5023 | PM5023 | A009 × PM5023 | PM5023 |
| 1 | 1170 | 1062 | 22.0 | 20.0 |
| 2 | 1280 | 722 | 22.0 | 21.0 |
| 3 | 1189 | 760 | 21.5 | 21.0 |
| 4 | 1574 | 979 | 23.0 | 21.0 |
| 5 | 1288 | 790 | 23.0 | 19.0 |
| 6 | 1036 | 730 | 22.0 | 19.0 |
| 7 | 1126 | 932 | 22.0 | 19.5 |
| 8 | 1500 | 1020 | 22.0 | 20.0 |
| 9 | 1228 | 906 | 21.0 | 20.0 |
| 10 | 1389 | 849 | 23.5 | 19.5 |
| Average | 1278.0 | 875.0 | 22.2 | 20.0 |
| Stan dev | 1.68E+02 | 1.23E+02 | 7.53E-01 | 7.82E-01 |
| T test | 8.74E-06 | | 4.92E-06 | |
| Probability % | 100.0 | | 100.0 | |
| % Difference | 46.1 | | 11.0 | |

TABLE 7

| Rep 1 | Head Weight (g) | | Head Circ (in) | |
|---|---|---|---|---|
| Sample # | A009 × PM5023 | A009 | A009 × PM5023 | A009 |
| 1 | 1209 | 1020 | 22.5 | 20.5 |
| 2 | 971 | 786 | 20.0 | 22.0 |
| 3 | 940 | 1041 | 20.5 | 22.0 |
| 4 | 864 | 782 | 20.0 | 21.0 |
| 5 | 1453 | 882 | 22.0 | 20.0 |
| 6 | 1280 | 844 | 22.0 | 20.0 |
| 7 | 1412 | 857 | 22.0 | 20.5 |
| 8 | 870 | 896 | 20.0 | 20.5 |
| 9 | 1288 | 970 | 21.0 | 22.0 |
| 10 | 983 | 1089 | 21.0 | 20.5 |
| Average | 1127.0 | 916.7 | 21.1 | 20.9 |
| Stan dev | 2.26E+02 | 1.08E+02 | 9.66E-01 | 8.10E-01 |
| T test | 1.60E-02 | | 6.22E-01 | |
| Probability % | 98.4 | | 37.8 | |
| % Difference | 22.9 | | 1.0 | |

| Rep 2 | Head Weight (g) | | Head Circ (in) | |
|---|---|---|---|---|
| Sample # | A009 × PM5023 | A009 | A009 × PM5023 | A009 |
| 1 | 1369 | 597 | 22.5 | 19.5 |
| 2 | 1099 | 1030 | 22.0 | 20.5 |
| 3 | 1142 | 1060 | 22.0 | 22.0 |
| 4 | 1007 | 838 | 21.0 | 21.0 |
| 5 | 984 | 837 | 21.0 | 20.5 |
| 6 | 1030 | 890 | 20.0 | 22.0 |
| 7 | 1205 | 742 | 22.0 | 19.5 |
| 8 | 1276 | 975 | 22.0 | 21.5 |
| 9 | 1005 | 638 | 21.0 | 19.5 |
| 10 | 1164 | 944 | 22.0 | 20.5 |
| Average | 1128.1 | 855.1 | 21.6 | 20.7 |
| Stan dev | 1.28E+02 | 1.57E+02 | 7.62E-01 | 9.73E-01 |
| T test | 4.83E-04 | | 3.35E-02 | |
| Probability % | 100.0 | | 96.7 | |
| % Difference | 31.9 | | 4.4 | |

| Rep 3 | Head Weight (g) | | Head Circ (in) | |
|---|---|---|---|---|
| Sample # | A009 × PM5023 | A009 | A009 × PM5023 | A009 |
| 1 | 1170 | 998 | 22.0 | 20.0 |
| 2 | 1280 | 503 | 22.0 | 19.0 |
| 3 | 1189 | 593 | 21.5 | 20.0 |
| 4 | 1574 | 775 | 23.0 | 20.0 |
| 5 | 1288 | 973 | 23.0 | 21.0 |
| 6 | 1036 | 830 | 22.0 | 20.0 |
| 7 | 1126 | 1006 | 22.0 | 21.0 |
| 8 | 1500 | 682 | 22.0 | 21.0 |
| 9 | 1228 | 1108 | 21.0 | 20.0 |
| 10 | 1389 | 740 | 23.5 | 21.0 |
| Average | 1278.0 | 820.8 | 22.2 | 20.3 |
| Stan dev | 1.68E+02 | 1.98E+02 | 7.53E-01 | 6.75E-01 |
| T test | 2.72E-05 | | 1.27E-05 | |
| Probability % | 100.0 | | 100.0 | |
| % Difference | 55.7 | | 9.4 | |

We claim:

1. A method for pollinating an emasculated or male sterile lettuce plant, comprising the steps of:
   a) providing a first lettuce plant comprising pollen;
   b) providing at least one emasculated or male sterile lettuce plant; and
   c) releasing *Megachile* bees, wherein said bees transfer pollen from said first lettuce plant to said emasculated or male sterile lettuce plant to pollinate said emasculated or male sterile lettuce plant.

2. The method of claim 1, wherein said *Megachile* bees are selected from the group consisting of: *Megachile rotundata, Megachile relativa*, and *Megachile pugnata* bees.

3. The method of claim 1, wherein said *Megachile* bees are *rotundata* bees.

4. The method of claim 1, wherein said first lettuce plant is an inbred or F1 lettuce plant and said providing comprises planting seed of said inbred or F1 lettuce plant wherein said seed germinates and grows into said inbred or F1 lettuce plant.

5. The method of claim 1 wherein said male sterile lettuce plant is a lettuce plant that does not produce pollen and said providing comprises planting seed of said male sterile lettuce plant wherein said seed germinates and grows into said male sterile lettuce plant.

6. The method of claim 1, wherein at least one emasculated lettuce plant is provided in step b).

7. The method of claim 1, wherein said emasculated lettuce plant is a plant comprising flowers with anthers wherein said plant is emasculated by removing the anthers or by misting.

8. The method of claim 1, wherein said step of releasing is performed in an open field.

9. The method of claim 1, wherein said step of releasing is performed in an enclosed or caged area.

10. The method of claim 1, wherein said first lettuce plant and said emasculated or male sterile plant flower during a flowering period, wherein said releasing step is performed by releasing a batch of bees on a weekly basis during the flowering period.

11. The method of claim 1, wherein said step of releasing is performed at a temperature of at least about 74° F.

12. The method of claim 1, wherein said lettuce plants are *Lactuca sativa* or *Lactuca Serriola* species.

13. The method of claim 1, wherein at least one male sterile plant is provided in step b).

14. A method for producing hybrid lettuce seed, comprising the steps of:
   a) providing a first lettuce plant comprising pollen;
   b) providing at least one emasculated or male sterile lettuce plant;
   c) releasing *Megachile* bees, wherein said bees transfer pollen from said first lettuce plant to said emasculated lettuce plant or said male sterile plant to form a pollinated lettuce plant; and
   d) growing said pollinated lettuce plant to produce hybrid lettuce seed.

15. The method of claim 14, wherein said *Megachile* bees are selected from the group consisting of *Megachile rotundata, Megachile relativa*, and *Megachile pugnata* bees.

16. The method of claim 14, wherein said *Megachile* bees are *Megachile rotundata* bees.

17. The method of claim 14, wherein said first lettuce plant is an inbred or F1 lettuce plant and said providing comprises planting seed of said inbred or F1 lettuce plant wherein said seed germinates and grows into said inbred or F1 lettuce plant.

18. The method of claim 14, wherein said male sterile lettuce plant is a lettuce plant that does not produce pollen and said providing comprises planting seed of said male sterile lettuce plant wherein said seed germinates and grows into said male sterile lettuce plant.

19. The method of claim 14, wherein said step of releasing is performed in an enclosed area or an open field.

20. The method of claim 14, wherein said first lettuce plant and said emasculated male sterile plant flower during a flowering period wherein said releasing step is performed by releasing a batch of bees on a weekly basis during the flowering period.

21. The method of claim 14, wherein said step of releasing is performed at a temperature of at least about 74° F.

22. The method of claim 14, wherein said lettuce plants are *Lactuca sativa* or *Lactuca Serriola* species.

23. The method of claim 19, wherein said step of releasing is performed in an enclosed area.

24. The method of claim 19, wherein said sept of releasing is performed in an open field.

25. The method of claim 14, wherein a male sterile plant is provided in step b).

26. The method of claim 14, wherein an emasculated plant is provided in step b).

* * * * *